(12) United States Patent
Meshberg

(10) Patent No.: US 10,744,520 B1
(45) Date of Patent: Aug. 18, 2020

(54) NASAL SPRAYER WITH CHILD RESISTANT SAFETY LOCK ASSEMBLY

(71) Applicant: Emil Meshberg, Fairfield, CT (US)

(72) Inventor: Emil Meshberg, Fairfield, CT (US)

(73) Assignee: Packaging Concepts Associates Holdings, Inc., Torrington, CT (US)

( * ) Notice: Subject to any disclaimer, the term of this patent is extended or adjusted under 35 U.S.C. 154(b) by 0 days.

(21) Appl. No.: 16/871,003

(22) Filed: May 10, 2020

Related U.S. Application Data

(63) Continuation-in-part of application No. 15/421,054, filed on Jan. 31, 2017, now Pat. No. 10,654,051.

(51) Int. Cl.
| | |
|---|---|
| B05B 1/02 | (2006.01) |
| B05B 11/00 | (2006.01) |
| A61F 9/00 | (2006.01) |
| A61M 11/00 | (2006.01) |
| B05B 7/00 | (2006.01) |
| B05B 1/26 | (2006.01) |
| B65D 83/14 | (2006.01) |
| B65D 83/22 | (2006.01) |
| B05B 15/65 | (2018.01) |

(52) U.S. Cl.
CPC .................. B05B 1/02 (2013.01); A61F 9/00 (2013.01); A61F 9/0008 (2013.01); A61F 9/0026 (2013.01); A61M 11/00 (2013.01); B05B 1/265 (2013.01); B05B 7/0012 (2013.01); B05B 11/0089 (2013.01); B65D 83/22 (2013.01); B65D 83/757 (2013.01); A61M 2210/0612 (2013.01); B05B 11/3059 (2013.01); B05B 15/65 (2018.02)

(58) Field of Classification Search
CPC ......... B05B 1/02; B05B 1/265; B05B 7/0012; B05B 11/0089; B05B 15/65; B05B 11/3059; A61F 9/00; A61F 9/008; A61F 9/0026; A61M 11/00; A61M 2210/0612; B65D 83/22; B65D 83/757
USPC ............ 239/329, 331, 333, 583; 222/153.04, 222/153.11, 153.13, 153.14, 321.6–321.9
See application file for complete search history.

(56) References Cited

U.S. PATENT DOCUMENTS

| | | | | |
|---|---|---|---|---|
| 4,944,429 A | * | 7/1990 | Bishop | ................ B05B 11/0027 222/153.13 |
| 5,282,551 A | * | 2/1994 | Pierson | ................ B65D 83/205 222/153.11 |

(Continued)

*Primary Examiner* — Steven J Ganey
(74) *Attorney, Agent, or Firm* — Glenn E. Gold, P.A.; Glenn E. Gold

(57) ABSTRACT

A child resistant nasal sprayer assembly includes a cap body having a base portion and an upstanding wall extending axially in an upward direction. An actuator is rotationally and axially slideably assembled within an interior of the upstanding wall. A safety button extends through the actuator and into a receiving notch formed in the upstanding wall. The safety button restricts motion of the actuator when placed in a locked configuration and enables motion of the actuator when placed in an unlocked configuration. The safety button is integral with a ring portion. The ring portion provides a biasing force to the button to retain the button in the locked position until purposely unlocked. Once unlocked, the operator compresses a pair of winglets, which operates a pump that dispenses medicinal composition stored within the bottle through a nozzle.

12 Claims, 11 Drawing Sheets

(56) References Cited

U.S. PATENT DOCUMENTS

| | | | | |
|---|---|---|---|---|
| 6,173,868 B1* | 1/2001 | DeJonge | ........... | A61M 15/0065 |
| | | | | 222/153.13 |
| 6,543,650 B1* | 4/2003 | Sprick | .................. | B65D 47/242 |
| | | | | 222/153.02 |
| 8,777,061 B1* | 7/2014 | Meshberg | ........... | B05B 11/3059 |
| | | | | 222/153.13 |
| 2002/0074429 A1* | 6/2002 | Hettrich | .............. | B05B 11/0044 |
| | | | | 239/333 |
| 2004/0026454 A1* | 2/2004 | Meshberg | ........... | B05B 11/0032 |
| | | | | 222/153.14 |
| 2008/0245896 A1* | 10/2008 | Welp | ................... | B05B 11/0032 |
| | | | | 239/333 |
| 2011/0133000 A1* | 6/2011 | Petit | ...................... | B05B 11/304 |
| | | | | 239/333 |
| 2015/0284177 A1* | 10/2015 | Patil | .................. | A61M 15/0001 |
| | | | | 222/153.04 |

* cited by examiner

NASAL SPRAYER WITH CHILD RESISTANT SAFETY LOCK ASSEMBLY

RELATED U.S. PATENT APPLICATIONS

This U.S. patent application is a continuation-in-part of U.S. non-provisional patent application Ser. No. 15/421,054, filed on Jan. 31, 2017, and issuing as U.S. Pat. No. 10,654,051 on May 15, 2020. The entire content of the '054 application is incorporated-by-reference herein.

FIELD OF THE INVENTION

The present disclosure generally relates to the field of product dispensing pumps. More particularly, the invention pertains to nasal sprayer devices incorporating child resistant safety closures.

BACKGROUND OF THE INVENTION

Various product dispensing pumps, sprayers and the like, incorporate safety features to prevent undesirable and/or unsafe dispensing of medicinal compositions. For instance, such safety features are commonly integrated into product packaging to prevent unintended dispensing of toxic, or otherwise harmful, compositions by children. In such cases, it is beneficial to incorporate a closure mechanism—such as cap or lid—into the dispensing container, which makes it exceedingly difficult for a child to toggle the closure mechanism from a locked state to an unlocked, dispensing state.

Various child-resistant closures are known. Many solutions incorporate respective configurations of threaded caps that cooperate with a corresponding container to prevent the twisting removal of the cap without first performing a secondary task to disengage a portion of the cap from a portion of the container. However, such threaded cap closures are not easily adapted for use with pump and aerosol dispensing containers. Accordingly, threaded safety cap mechanisms are inadequate for various types of medicinal composition dispensers, such as inhalers, nasal sprayers, dispensing pumps and the like.

Another known approach incorporates a single use locking mechanism configured to provide a product user with visible evidence of product tampering. In this case, the child resistant locking mechanism, or feature, is generally only applicable during an initial use of the product; providing no protection against subsequent access to the contained medicinal composition.

In accordance with yet another known dispensing container locking solution, a pump assembly is attached to, or integrated with, a bottle. In this case, a pump actuator is provided to operate the pump in order to dispense a composition housed within the bottle. The pump actuator assembly includes a dispensing actuator locking interface, which governs vertical motion of the pump actuator. The dispensing actuator locking interface includes a projecting locking feature extending outward from an upper portion of the pump actuator. The projecting locking feature is retained in a locked configuration via an engagement edge of an actuator control feature. The projecting locking feature may be disengaged from the actuator control feature by rotating the pump actuator. Rotation of the pump actuator is restricted by a hinged rotation locking member extending outward from the pump actuator. The rotation locking member engages a locking wall, wherein the locking wall is in the form of a vertical edge provided in an upstanding wall circumscribing the pump actuator. However, the rotation locking member configuration has several limitations. In this case, the rotation locking member is an integral feature of the pump actuator, formed during a common molding process. The rotation locking member is hingedly attached to the pump actuator by a living hinge. This configuration risks damage to the hinge; to wit, the rotation locking member may become detached from the pump actuator. Once the rotation locking member has become detached it no longer provides the intended locking function. Since the pump actuator and rotation locking member are fabricated having a uniform construction, the material selection for each feature is not optimized. The hinge portion requires a high spring constant and reduced brittle nature to ensure that it does not break with minimal elastic deformation, whereas the pump actuator portion requires a more rigid material. The design of the rotation locking member—including geometry, size and location—is limited by the inclusion of the hinge. The design limitations restrict the effectiveness of the rotation locking member. This also contributes to the correspondingly high degree of force required to adequately depress the locking member. Users having limited strength, hand dexterity, mobility and the like, may have difficulty applying the degree of force necessary to depress the locking member. Since the pump actuator and rotation locking member are fabricated having a uniform, one-piece construction they are manufactured from a common, single-colored material. The incorporation of a common color makes it exceedingly difficult for an end user to visually distinguish the pump actuator from the rotation locking member. In that manner, the uniform color acts to visibly camouflage, or conceal, the rotation locking member. This is particularly problematic for sight impaired individuals, such as the elderly.

Another common drawback with existing safety/locking closures—particularly those found in dispensing containers intended for nasal delivery of medicinal compositions—is inefficient application of the dispensed nasal medication. For instance, some nasal medications require independent, direct application to each nostril.

Efforts have been made to provide an improved child-resistant actuator for use with a nasal sprayer, which overcomes the various drawbacks, disadvantages, and limitations of the prior art. However, such efforts have not been met with significant success. Consequently, the need remains for an improved child-resistant actuator, which provides reliable locking of the actuator to prevent undesired dispensing of the medicinal composition, enables the use of replaceable components between the locking feature and the primary components of the closure, and provides a convenient cost-effective means to color code various elements of the child-resistant closure.

BRIEF SUMMARY OF THE INVENTION

The basic inventive concept provides a child-resistant locking interface that restricts operation of a dispensing element of a container, and provides an improved nozzle extension for efficient application of the product. The locking interface is constructed to prevent unintended dispensing of container contents by a child, while facilitating the incorporation of a design having optimized geometries and fabrication of different materials for the various components.

In accordance with an exemplary implementation, a child resistant nasal sprayer assembly is provided comprising:

a bottle having a body defined by a cylindrical sidewall having a lower end and an opposite upper end, a bottom wall having a periphery contiguous with the cylindrical sidewall lower end, the sidewall upper end defining a bottle body opening, the bottle body defining an interior bottle space containing a dispensable composition;

an actuation safety lock member in the form of a C-shaped body extending between a proximal end and a distal end, a push button feature protruding radially outward from an exterior, convex surface proximate to the proximal end of the C-shaped body, wherein, during use, the structure of the actuation safety lock member enables inward radial flexure along a flexion length of the C-shaped body between the push button feature and the distal end;

a rotatable and compressible dispensing actuator including a central body portion in the form of a cylindrical sidewall having an interior sidewall surface and an opposite exterior sidewall surface, the dispensing actuator central body cylindrical sidewall transitioning, at an upper end thereof, to a dispensing actuator upper wall, the dispensing actuator upper wall transitioning radially inward to a dispensing actuator nozzle having a central dispensing actuator nozzle orifice, a pair of actuator wings extending radially outward from the exterior sidewall surface of the central body portion, the pair of actuator wings circumferentially offset from one another, the central body cylindrical sidewall having an opening extending completely therethrough, the opening sized and shaped to enable extension of the push button feature of the safety lock member therethrough when the dispensing actuator is in a child-resistant locked position, the opposite proximal and distal ends of the safety lock member C-shaped body each bearing against respective edges of a raised safety lock member retention feature protruding radially inward from the interior surface of the central body portion cylindrical sidewall, the exterior surface of the safety lock member C-shaped body flexion length between the push button feature and the distal end bearing against the interior surface of the central body portion cylindrical sidewall when the dispensing actuator is in said child-resistant locked position;

a bottle cap having a base section and an upper section adjoined by an annular transition wall having a plane oriented transverse to a common central axis of the base section and the upper section, the base section having a cylindrical sidewall secured at a lower end thereof about the bottle opening, the annular transition wall defining a central aperture, the upper section of bottle cap having a cylindrical sidewall terminating at an upper edge, the upper edge defining a stepped first notch and a second notch circumferentially offset from the stepped first notch; and a dispensing pump subassembly extending from within the interior bottle space, through the central opening in the bottle cap annular transition wall, and into an interior of the dispensing actuator, the dispensing pump subassembly arranged and configured to dispense a volume of the dispensable composition contained within the bottle body interior space, wherein, upon applying a push button release force to a push button contact surface of the actuation safety lock member C-shaped body, and subsequently rotating the dispensing actuator in a direction toward a lowermost notch of the bottle cap stepped first notch, wherein the dispensing actuator is in an unlocked state, the dispensing actuator may be freely compressed to communicate a volume of the dispensable composition from the interior bottle space, through the dispensing pump subassembly, for emission through an opening of the dispensing actuator nozzle.

In some implementations, the dispensing actuator wings may be circumferentially offset 180° from each other.

In some implementations, each one of the pair of dispensing actuator wings may extend outwardly from the exterior sidewall surface of the central body portion to define an actuator wing radiused edge.

In some implementations, the exterior surface of the dispensing actuator central body portion cylindrical sidewall is maintained in frictional engagement with an interior surface of the upper section cylindrical sidewall.

In some implementations, during a composition dispensing operation, the lower edge of the dispensing actuator cylindrical sidewall may engage an upper surface of the bottle cap transverse annular wall to limit downward translation of the dispensing actuator.

In some implementations, the push button portion of the actuation safety lock member C-shaped body may transition to the push button contact surface via a tapered facet.

In some implementations, upon concurrently depressing the push button inwardly and rotating the dispensing actuator from a locked position to an unlocked position, compression of the flexion length of the actuation safety lock member C-shaped body may urge flexure of the flexion length.

In some implementations, upon rotating the dispensing actuator back from the unlocked position to the child resistant locked position, the flexion length of the actuation safety lock member C-shaped body may be decompressed and the push button portion urged outwardly through the opening in the cylindrical sidewall of the dispensing actuator.

In some implementations, the dispensing actuator cylindrical sidewall may be slidably and rotationally assembled to the cylindrical upper section of the bottle cap, wherein, in operation, the safety lock member push button may be depressed to clear the interior surface of the cylindrical sidewall of the bottle cap upper section, thereby enabling rotation of the dispensing actuator relative to the bottle cap, to a position urging the safety lock member push button against the interior surface of the bottle cap upper section cylindrical sidewall to enable downward axial translation of the dispensing actuator upon application of a compressive force to upper surfaces of the respective dispensing actuator wings, the compression causing the dispensing actuator to slide downwardly within the bottle cap upper section to engage the dispensing pump and thereby discharge a volume of the composition, in the form of a mist, through the dispensing actuator nozzle orifice.

In some implementations, the pair of wings may further comprise respective planar wing compression contact surfaces oriented perpendicular to a central axis of the child resistant nasal sprayer assembly.

In some implementations, the dispensing pump subassembly (or alternative means, such as a metered dose aerosol valve) may supported by the bottle cap.

In some implementations, the dispensing pump subassembly may be supported by a vertically-oriented annular wall disposed about a perimeter of the central opening in the bottle cap annular transition wall and extending upwardly from the upper surface of the bottle cap annular transition wall.

These and other advantages of the invention will be further understood and appreciated by those skilled in the art by reference to the following written specification, claims and appended drawings.

BRIEF DESCRIPTION OF THE DRAWINGS

The components in the drawing figures are not necessarily to scale, emphasis instead being placed upon illustrating the principles of the invention. The invention will now be described, by way of example, with reference to the accompanying drawing figures, in which.

In the accompanying figures, reference numerals designate corresponding elements throughout the different views of the drawings.

DETAILED DESCRIPTION OF EXEMPLARY IMPLEMENTATIONS

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. In other implementations, well-known features and methods have not been described in detail so as not to obscure the invention. For purposes of description herein, the terms "upper", "lower", "left", "right", "front", "back", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments that may be disclosed herein are not to be considered as limiting, unless the claims expressly state otherwise.

Figure 3:
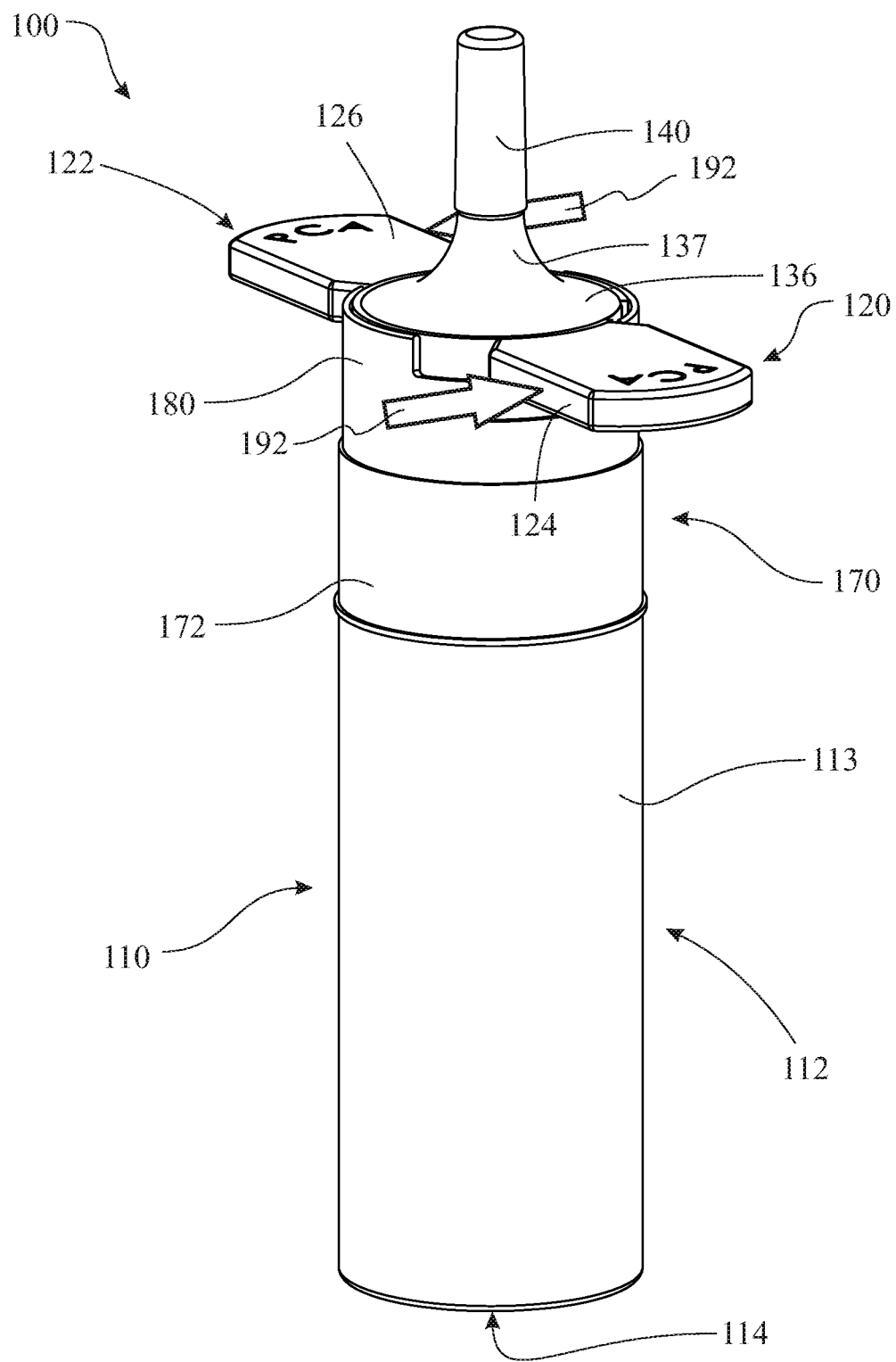
FIG. 3 is an isometric view of the CR nasal sprayer assembly originally introduced in FIG. 1, illustrating the application of a rotational force applied to edges 124 of wings 122 of a dispensing actuator 120, to thereby toggle the safety lock push button from a locked position/state (FIG. 2) to an unlocked position/state.
Figure 4:
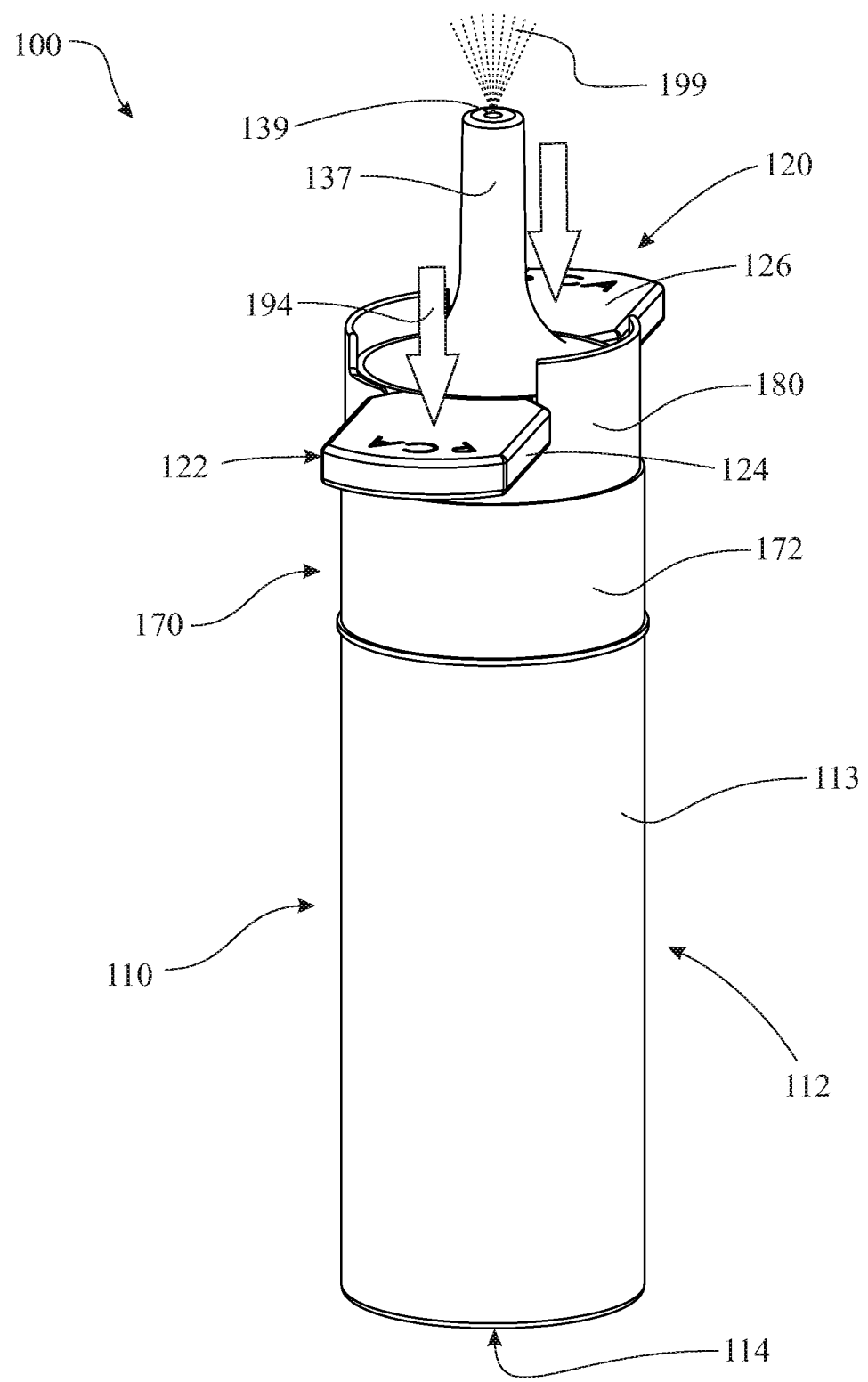
FIG. 4 is an isometric view of the CR nasal sprayer assembly shown in FIG. 3, illustrating the subsequent application of a compression force to a compression contact surface 126 of the wings 122 of dispensing actuator 120, to dispense a predetermined dose/volume of a medicinal composition from bottle 110.
Figure 5:
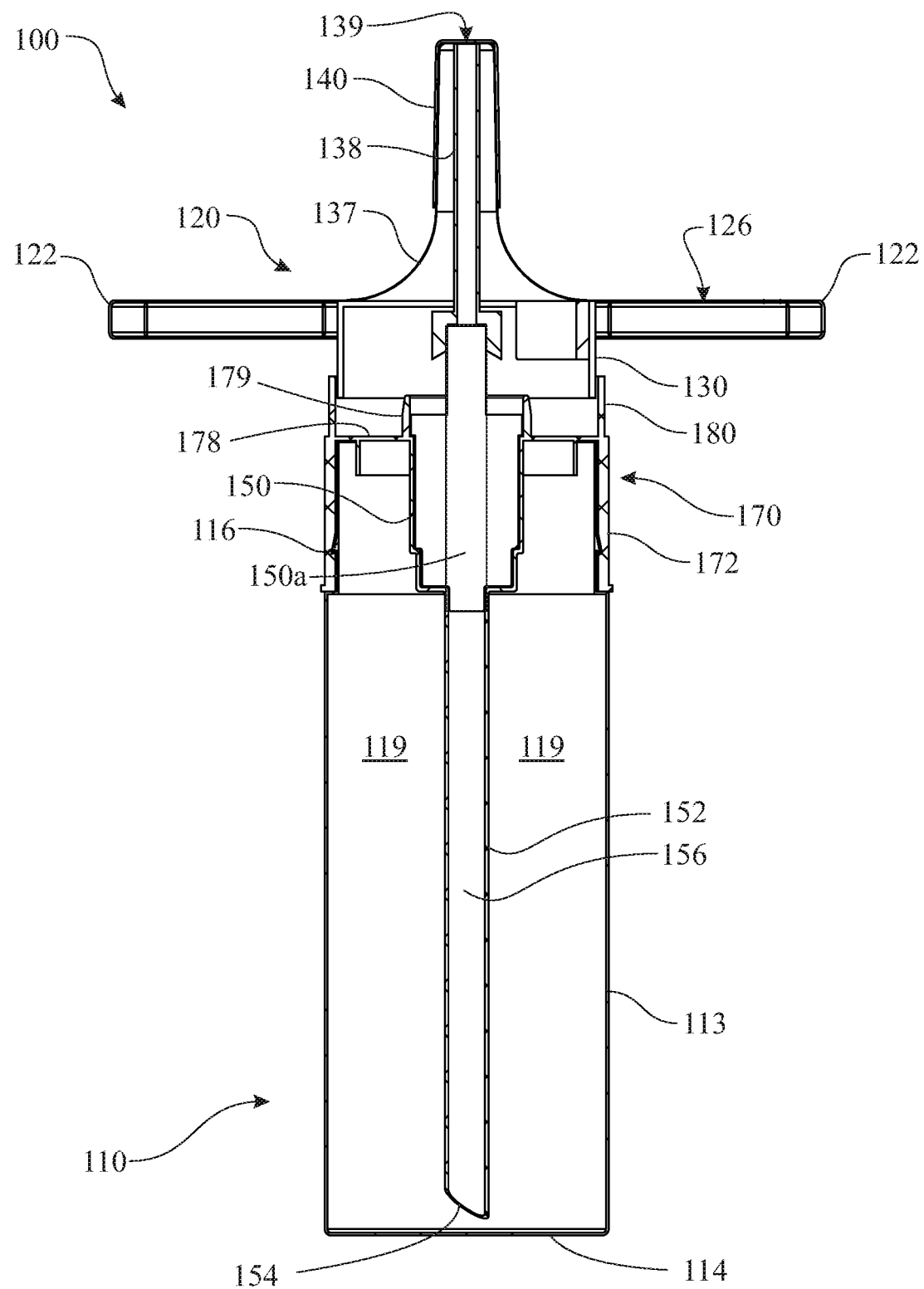
FIG. 5 is a cross-sectional view taken along a central axis of the CR nasal sprayer assembly originally introduced in FIG. 1, showing some internal structural details of the nasal sprayer assembly in a child-resistant, locked state.
Figure 6:
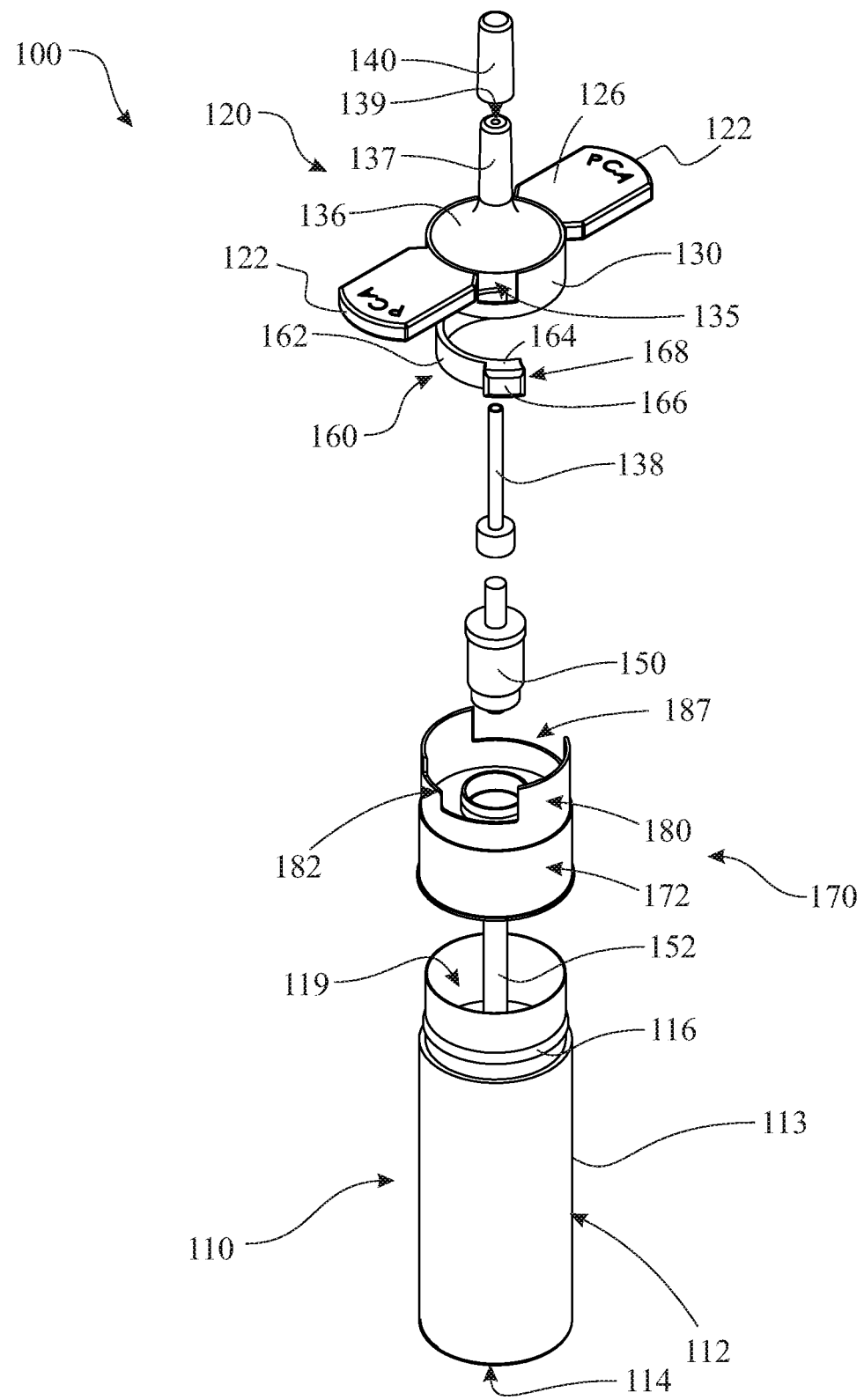
FIG. 6 is an isometric exploded view of the CR nasal sprayer assembly originally introduced in FIG. 1.
Figure 7:
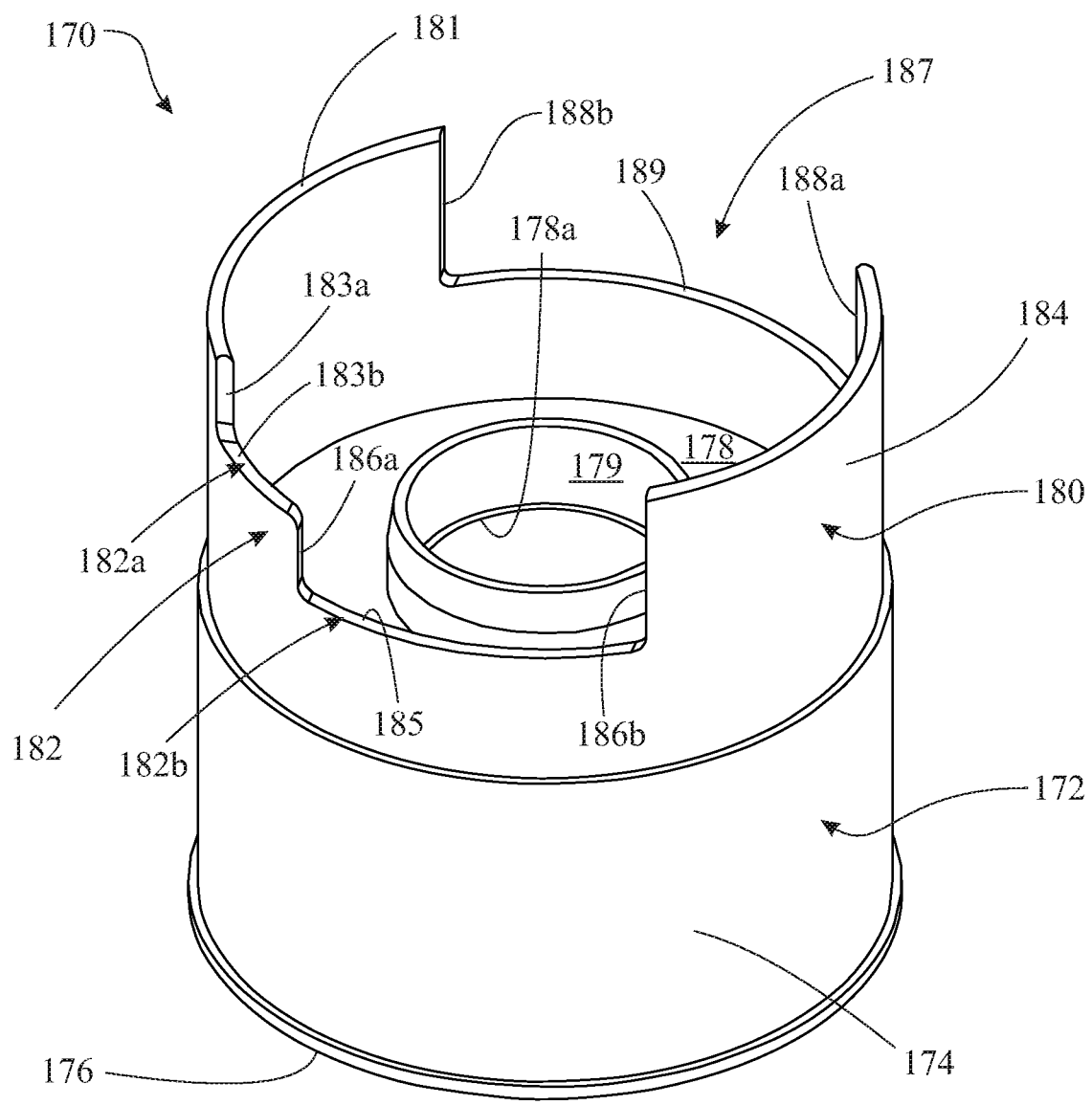
FIG. 7 is an enlarged isometric view of an exemplary bottle cap 170 of the CR nasal sprayer assembly originally introduced in FIG. 1.
Figure 8:
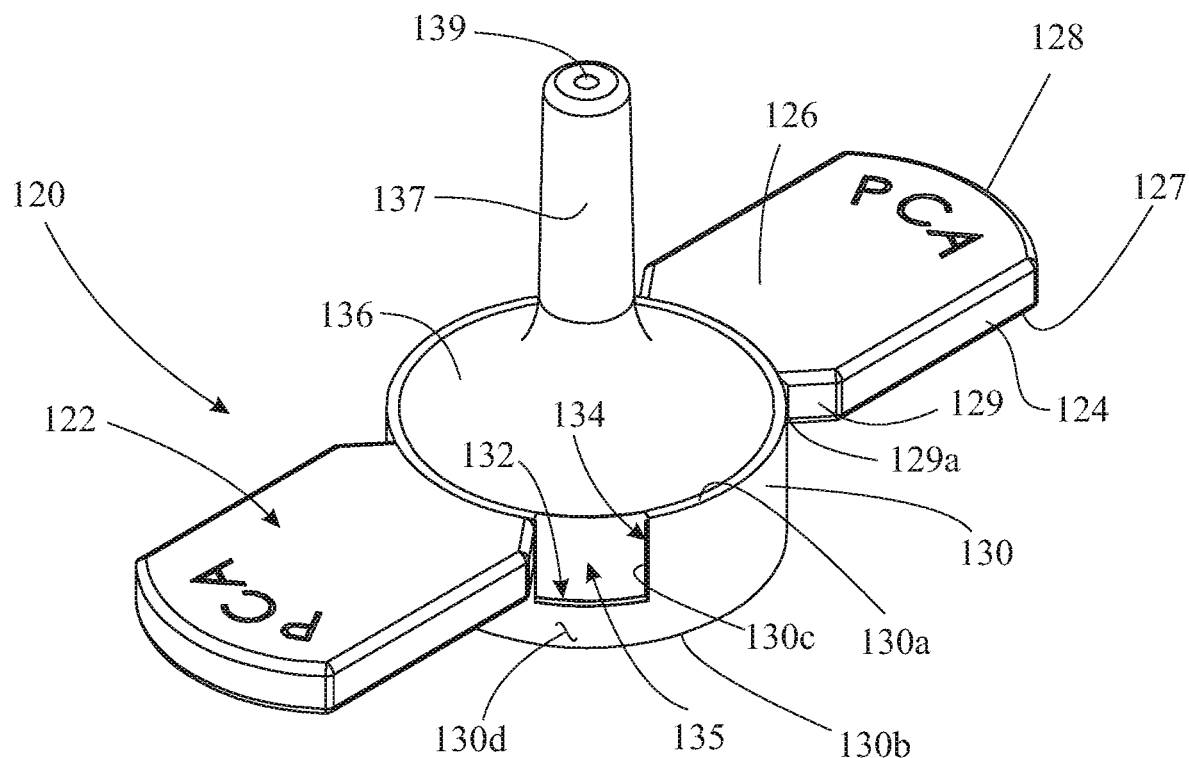
FIG. 8 is an enlarged isometric view of an exemplary rotatable and compressible dispensing actuator 120 of the CR nasal sprayer assembly originally introduced in FIG. 1.
Figure 9:
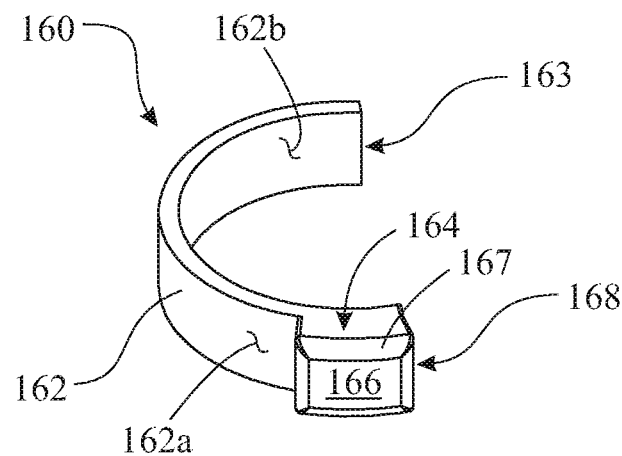
FIG. 9 is an enlarged isometric view of an exemplary actuation safety lock member 120 of the CR sprayer assembly originally introduced in FIG. 1.
Figure 10:
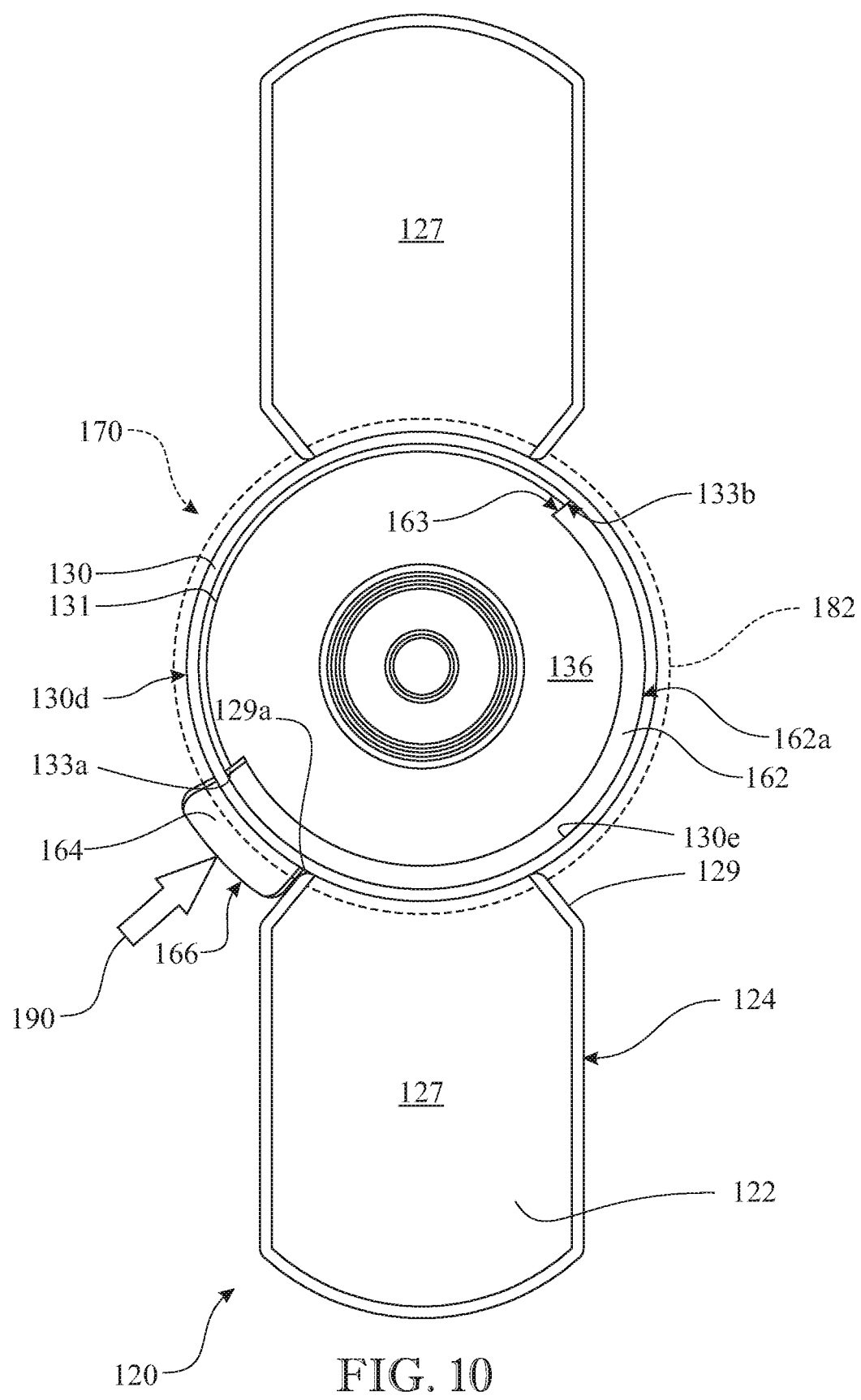
FIG. 10 is a bottom view of the actuation safety lock member 160 operatively assembled within a central portion of the dispensing actuator 120, wherein the safety lock member is shown in a child-resistant locked position.
Figure 11:
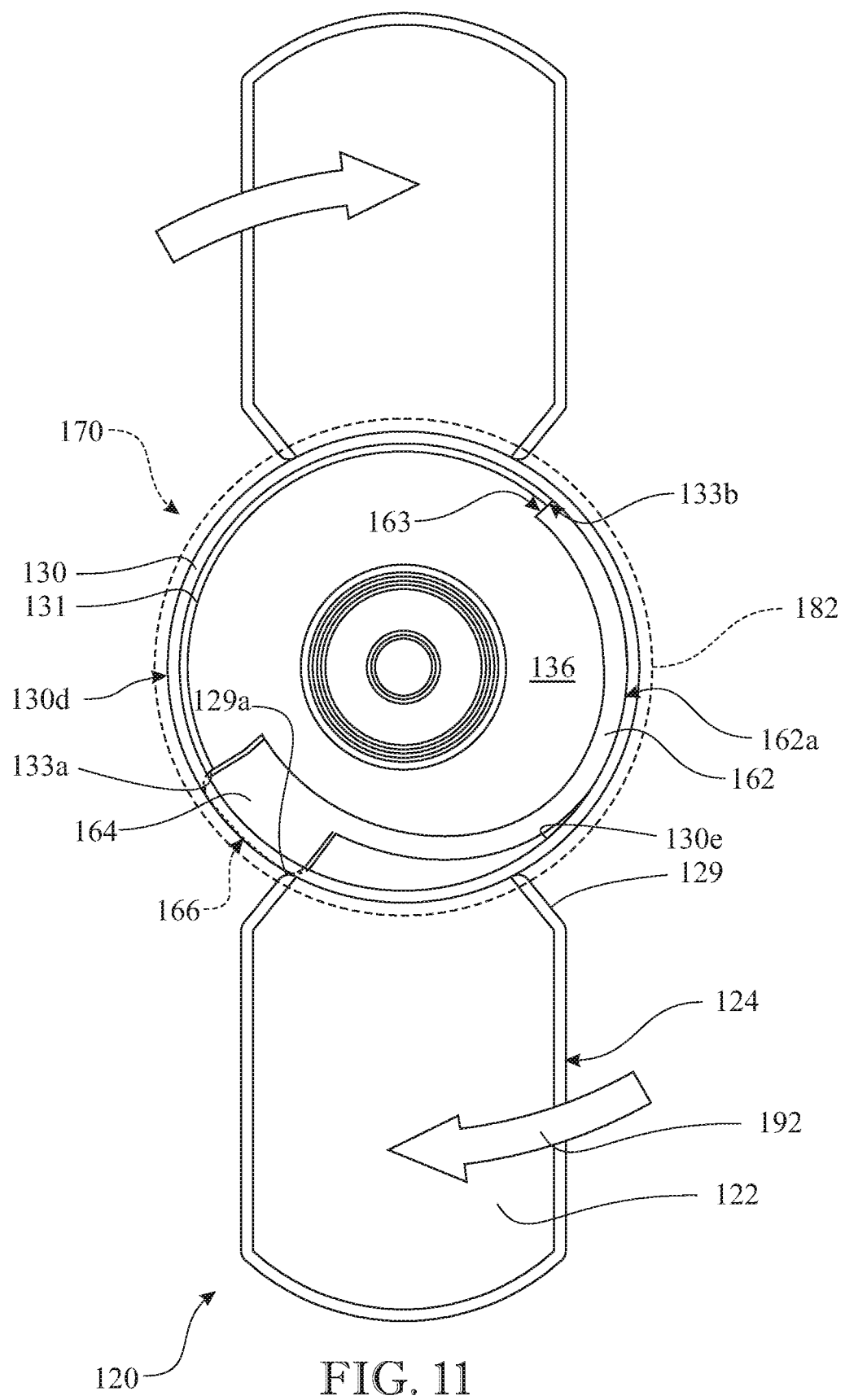
FIG. 11 is a bottom view of the actuation safety lock member 160 operatively assembled within a central portion of the dispensing actuator 120, wherein the safety lock member is shown with push button 164 fully depressed to enable subsequent rotation of the dispensing actuator 120 to an unlocked position.
Figure 12:
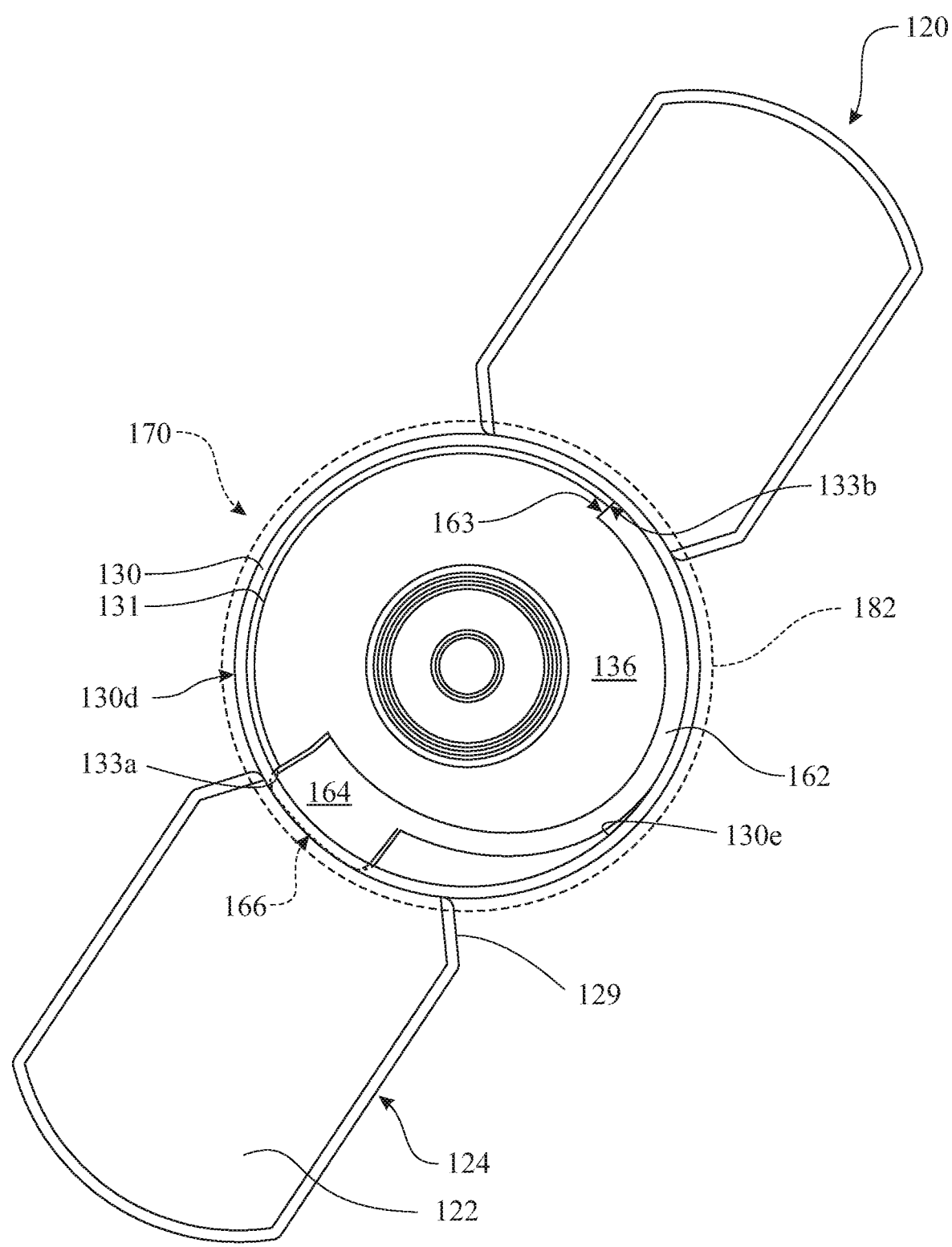
FIG. 12 is a bottom view of the actuation safety lock member 160 operatively assembled within a central portion of the dispensing actuator 120, wherein the safety lock member is shown with push button 164 fully depressed, and the dispensing actuator 120 has been rotated to the unlocked position, wherein the dispensing actuator may be compressed to emit a metered spray dosage of the contained medicinal composition.

Referring now generally to FIGS. 1-12, a child resistant (CR) nasal sprayer assembly 100 is shown in accordance with an exemplary implementation of the present invention. In FIGS. 1-4, the CR nasal sprayer assembly 100 is shown in a fully-assembled operative condition, with the series of figures illustrating successive operational steps required to unlock and use the CR nasal sprayer. In FIGS. 5-6, cooperative relationships of the various components and features of the CR nasal sprayer assembly 100 are shown. In FIGS. 7-9, individual bottle cap 170, dispensing actuator 120, and actuation safety lock member 160 components of the CR nasal sprayer assembly 100 are shown in greater detail. In FIGS. 10-12, the interaction of the aforementioned bottle cap 170, dispensing actuator 120 and actuation safety lock member 160 components are illustrated undergoing a series of steps during which the CR nasal sprayer assembly 100 is transitioned from a "locked" state/condition to an "unlocked" state condition.

The CR nasal sprayer assembly 100 incorporates a safety locking feature generally comprising a rotatable and compressible safety lock member 160 installed within an interior of a selectively rotatable and compressible dispensing actuator 120, wherein the safety lock member 160 cooperatively engages with features of a bottle cap 170 to enable an adult user to selectively control rotational and compressive translation of the dispensing actuator 120 vis-a-vis the bottle cap 170, thereby selectively toggling the CR nasal sprayer assembly 100 between an inoperable, locked configuration and an operable, unlocked configuration. In this manner, an adult user can very simply lock the dispensing actuator when the assembly is not being used, to prevent a young child from dispensing a composition contained within an assembly bottle 110.

The CR nasal sprayer assembly 100 functions as a delivery system for the discharge of predetermined spray dosage of a medicinal composition from a volume of medicinal composition stored within an interior volume 119 of a bottle body 112. The bottle interior volume 119 is defined by a bottle body cylindrical sidewall 113, a bottle body bottom wall 114, and a horizontally-oriented, transverse annular wall 178 of bottle cap 170. As used herein, the term "horizontally-oriented" is meant to denote an annular wall 178 oriented transversely with respect to a longitudinal/vertical axis of the CR nasal sprayer assembly. An opening is provided at an upper end of bottle cylindrical body 112 opposite bottom wall 114. A bottle cap locking feature 116 (FIG. 5) may be integrated into a cylindrical sidewall 113 of an uppermost portion of bottle body 112 proximate to the open end thereof. For example, as best shown in FIG. 6, the bottle cap locking feature may be provided as an annular boss 116 formed during fabrication of the bottle body 112. As will be readily apparent to those skilled in the relevant arts, the bottle cap locking feature 116 of bottle body 112 may comprise any suitable mechanical assembly form factor, including, a single helical threading, a series of helical threading, a cam, or a twist-and-lock configuration, to name just a few.

Bottle cap 170 preferably has a unitary, molded construction including a bottle cap base section 172 and a bottle cap upper section 180 contiguous therewith. The bottle cap base section 172 includes features enabling assembly of the bottle cap 170 and the bottle 110 to one another. The bottle cap base section 172 may be slidably assembled over the open upper end of the cylindrical sidewall 113 of bottle body 112. In particular, the bottle cap 170 may be secured to the cylindrical bottle body 112 by snapping the cap locking feature 116 into a mating recess (not shown) or other suitable receiving and retention formation provided on an interior surface of the bottle cap base section 172, as shown in FIG. 5. A dip tube 152 may be provided integral with (e.g. as a molded feature of) or, alternatively, assembled to, the bottle cap 170. The dip tube 152 defines a dip tube passageway 156 for communicating a medicinal composition from the interior 119 of bottle body 112 toward a dispensing pump subassembly 150 (or alternative mechanism, such as a metered dose aerosol valve). In particular, a volume of contained fluid composition from bottle interior space 119 enters dip tube passageway 156 through a pick-up orifice 154 located at a distal end of the dip tube, and is communicated into dispensing pump subassembly 150, which is in fluid communication with dip tube passageway 156. Referring briefly to FIG. 5, although individual components of dispensing pump subassembly 150 are not shown, the internal structures of various commercially-available nasal dose dispensing pumps are well known in the relevant art. Preferably, dispensing pump subassembly 150 is a Valois-type nasal dose dispensing pump. It will be readily apparent to those skilled in the art that although the exemplary implementation of the present invention incorporates a nasal dose dispensing pump mechanism, any known alternative mechanism for communicating a metered dose of medicinal composition within a nasal sprayer may be incorporated without departing from the intended scope of the invention. Again, by way of example, a metered dose aerosol valve could be easily incorporated in lieu of a pump mechanism. Accordingly, the term "dispensing pump" as used herein should be broadly interpreted to cover any available composition driving mechanism conventionally incorporated into nasal sprayer devices.

As will be readily apparent to those skilled in the relevant art, the inner structure of such conventional dispensing pumps, metered dose aerosol valves, and the like, is not necessary for a complete understanding of the present invention. That is, one skilled in the art of nasal sprayers would readily be able to construct the present invention using available alternative metered dose delivery mechanisms. Subsequently, the composition dosage volume is communicated from the dispensing pump subassembly 150 into dispensing nozzle stem extension 138 for emission as a spray, or mist, through nozzle orifice 139. The dispensing pump subassembly 150 may be assembled to, and retained by, the bottle cap 170.

Referring now primarily to FIG. 7, bottle cap 170 generally includes a base section 172 and contiguous upper section 180 separated interiorly by a horizontally-oriented, transverse annular wall 178. Transverse annular wall 178 defines a central opening 178a, which is circumscribed by a vertically-oriented interior annular wall 179 extending upwardly from an upper surface of the horizontally-oriented transverse annular wall.

Base section 172 is at least partially defined by a cylindrical sidewall 174 terminating at a base section lower edge 176. Similarly, upper section 180 is at least partially defined by a corresponding upper section cylindrical sidewall 184 terminating at an upper edge 181, wherein upper section cylindrical wall 184 is contiguous with base section cylindrical sidewall 174. Upper edge 181 of cylindrical sidewall 184 has a stepped first notch 182 provided therein. Furthermore, upper edge 181 has a (preferably, non-stepped) second notch 187 provided therein, wherein stepped first notch 182 is circumferentially spaced-apart from, or radially offset from, corresponding second notch 187.

Stepped first notch 182 includes a first, shallow stepped portion 182a defined by a first vertical edge 183a and a first horizontal edge 183b, and a second, deep stepped portion 182b defined by a second vertical edge 186a, a third vertical edge 186b and a second horizontal edge 185 spanning the second and third vertical edges. Significantly, the stepped configuration of first notch 182 functions to limit both rotational translation and axial translation of dispensing actuator 120. In particular, first vertical edge 183a functions as a rotational stop limit to resist clockwise rotation of dispensing actuator 120 via engagement with a corresponding wing rotational actuation contact edge 124; particularly, when the dispensing actuator is in a locked position and push button 164 of C-shaped actuation safety lock member 160 has been depressed. Likewise, first horizontal edge 183b functions as an axial stop limit to resist downward movement, or translation, of dispensing actuator 120 via engagement with a corresponding wing lower surface 127; particularly, when the dispensing actuator is in a locked position but push button 164 of C-shaped actuation safety lock member 160 has been depressed (for example, as depicted in FIG. 11). In similar fashion, second and third vertical edges, 186a and 186b, respectively, function to resist both clockwise and counterclockwise rotation of dispensing actuator 120 while in an unlocked and compressed position (for example, as depicted in FIG. 4), and second horizontal edge 185, spanning the second and third vertical edges, functions as an axial stop limit to the downward translation, or compression, of the dispensing actuator while in an unlocked, compressible position (for example, as depicted in FIG. 3).

Second notch 187, positioned to surround a second one of the circumferentially-offset pair of wings 122, is defined by fourth and fifth vertical edges, 188a and 188b, respectively, and third horizontal edge 189 spanning the fourth and fifth vertical edges. Fourth vertical edge 188a acts as a clockwise rotation stop limit for dispensing actuator 120, working in concert with first vertical edge 183a. Fifth vertical edge 188b acts as a counterclockwise rotation stop limit for dispensing actuator 120, working in concert with third vertical edge 186b. Third horizontal edge 189, working in concert with second horizontal edge 185, acts as a stop limit to the downward translation, or compression, of dispensing actuator 120 when the dispensing actuator is in a compressible, unlocked position.

Referring now particularly to FIG. 8, dispensing actuator 120 is generally defined by a central dispensing actuator body having a pair of circumferentially-offset, or radially-offset, wings 122 extending radially-outward therefrom. In particular, the central dispensing body is defined by a dispensing actuator cylindrical sidewall 130 extending between an upper actuator cylindrical sidewall edge 130a and a lower actuator cylindrical sidewall edge 130b, wherein the upper sidewall edge transitions to a dispensing actuator upper wall 136, which, in turn, transitions concentrically inward to define a composition-dispensing nozzle 137 having a nozzle orifice 139. Dispensing actuator cylindrical sidewall 130 is further defined by an exterior cylindrical sidewall surface 130d and an opposite interior cylindrical sidewall surface 130e (FIG. 10). Each of the pair of wings 122 projects radially outward from an upper portion of sidewall 130 adjacent to sidewall upper edge 130a. Preferably, the wings 122 are provided 180° circumferentially offset, or radially offset, from one another. Each of the wings 122 is generally defined by a pair of opposite rotation actuation contact edges 124, an arcuate distal edge 128 spanning the rotation actuation contact edges, an upper compression contact surface 126, and a lower surface 127. Furthermore, each wing rotation actuation contact edge 124 transitions to an inwardly-tapered edge 129 adjoined to dispensing actuator cylindrical sidewall 130 at a radiused edge portion 129a. A dispensing actuator cylindrical sidewall opening, or notch 130c, defines a safety lock member push button-receiving opening 135, or push button passageway, extending through dispensing actuator cylindrical sidewall 130 directly adjacent to a proximal end of one of the pair of wings 122. Push button receiving opening 135 has a shape substantially conforming to the cross-sectional shape of push button portion 164, and is sized nominally larger than the push button portion to enable it to protrude therethrough in a locked condition.

Referring now particularly to FIG. 9, actuation safety lock member 160 is preferably provided in the form of a unitary C-shaped spring body 161 having an integral push button portion 164 at a proximal end 168 thereof, and having a flexion length 162 extending between the push button portion and a distal end 163 of the C-shaped spring body. The flexion length 162 has a convex exterior surface 162a and an opposite concave interior surface 162b. The push button portion 164 transitions, via push button facets 167, to a push button contact surface 166 (alternatively referred to herein as a release force surface). Preferably, push button 164 has a convex, radiused contact surface 166 that substantially conforms to the corresponding interior concave surface 130e of dispensing actuator cylindrical sidewall 130. As further elucidated below, the conforming surfaces enable and facilitate sliding engagement between radiused contact surface 130e of push button 164 and interior surface 130e of dispensing actuator cylindrical sidewall 130, during rotation of dispensing actuator 120 from a locked position (FIG. 1) to an unlocked position (FIG. 3).

Referring now generally to FIGS. 1-12, and more particularly to FIGS. 10-12, the dispensing actuator 120 is slideably and rotationally assembled to the upper section 180 of bottle cap 170. The dispensing actuator 120 may include one or more features to aid in the assembly of the dispensing actuator to one or more mating features of the dispensing pump assembly 150, as best shown in FIG. 5. Prior to inserting the cylindrical sidewall 130 of the dispensing actuator 120 into the upper section 180 of bottle cap 170, actuation safety lock member 160 is seated within an interior space defined by the dispensing actuator cylindrical sidewall 130, as best shown in FIG. 10. Operational clearances on the upper section 180 of bottle cap 170 are provided to engage the locking features that bias the child resistant nasal sprayer assembly 100 into a locked condition, and to enable rotation (and subsequent compression) of the dispensing actuator 120, to dispense a metered dose of a contained composition, when the child resistant nasal sprayer assembly is biased into an unlocked condition.

Figure 1:
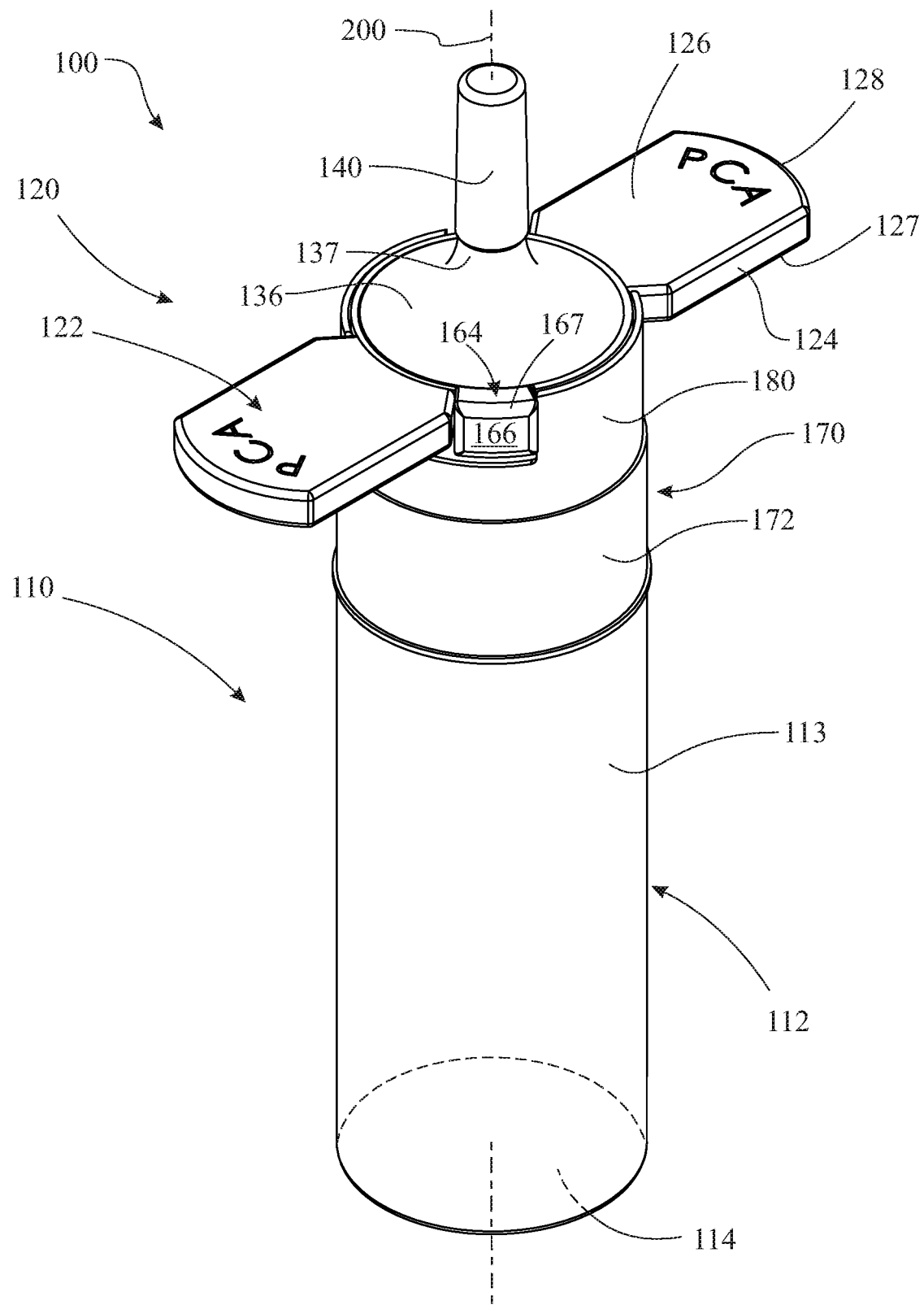
FIG. 1 is an isometric view of a fully assembled exemplary child resistant (CR) nasal sprayer assembly shown in a child-resistant locked state, in accordance with the present invention.

As previously described with reference to the bottle cap 170 (FIG. 7), a first shallow step 182a of the stepped first notch 182 is defined by wing vertical compression-resisting horizontal edge 183b and clockwise rotation-resisting horizontal edge 183a. The first shallow step 182a functions as a wing storage notch while the dispensing actuator 120 is in the locked, child-resistant position (FIG. 1). A second, deeper step 182b of the stepped first notch 182 is defined by wing clockwise rotation-resisting second vertical edge 186a, wing counterclockwise-resisting third vertical edge 186b, and wing vertical, or axial, compression stop limit edge 185.

The first and second steps, 182a and 182b, respectively, of stepped first notch 182 are contiguous, enabling the dispensing actuator wings 122 to seamlessly transition between the first, shallow step 182a (alternatively referred to as a wing storage notch) and the second step (alternatively referred to as a wing actuation enabling notch) when the dispensing actuator 120 is rotated with respect to the bottle cap 170. Second notch 187 (alternatively referred to herein as an operational clearance notch) is provided at a position along the sidewall of upper section 180 that is 180 degrees offset from the stepped first notch 182. As will be apparent to those skilled in the relevant art, the second notch 187, or operational clearance notch, while shown having a different geometry than stepped first notch 182, may be designed to replicate the stepped first notch. For that matter, the second notch 187 may incorporate any of a number of alternative geometries, or configurations, without departing from the intended scope of the invention. As previously described, the bottle cap 170 may include a pump retention feature 179 particularly configured to receive and retain the dispensing pump assembly 150.

Dispensing components include the dip tube 152, which is in fluid communication with a supply end of the dispensing pump assembly 150, and a stem extension 138 in fluid communication with a dispensing end of the dispensing pump assembly 150. The stem extension 138 extends upwards into an interior of the medicine dispensing nozzle 137, preferably locating a dispensing end of the stem extension 138 proximate or against a nozzle orifice 139 of the medicine dispensing nozzle 137. A mechanical break up can be integral in the top of the stem extension 138, excluding a requirement for a spray insert. Composition dispensing nozzle 137 extends vertically upwards along central axis 200 from a central location on the actuator upper wall 136 of the dispensing actuator 120. A dust cap 140 may be employed to prevent the ingress of undesirable contaminants into the dispensing nozzle 137. The dust cap 140 may be secured by friction, utilization of a bossed ring formed about a base of the medicine dispensing nozzle 137, and the like.

Referring now particularly to FIGS. 10-12, the interaction of the bottle cap 170, dispensing actuator 120 and actuation safety lock member 160 components are shown undergoing a series of steps during which the CR nasal sprayer assembly 100 is transitioned from a locked, child-resistant state (FIG. 10) to an unlocked, dispensing state (FIG. 12) enabling metered dosage dispensing of a medicinal composition contained within bottle 110.

In FIG. 10, a bottom view of the actuation safety lock member 160 operatively assembled within a central portion of the dispensing actuator 120 is shown in an initial locked, child-resistant state. In this configuration, the following conditions hold true: (a) safety lock push button portion 164 of actuation safety lock member 160 protrudes through the safety lock member push button receiving opening 135, such that a first lateral side of the push button portion bears against inwardly-tapered edge 129 of wing 122; (b) exterior surface 162a of C-shaped body flexion length 162 bears against the interior surface 130e of dispensing actuator cylindrical sidewall 130; (c) safety lock member push button receiving opening 135 overlies first shallow step 182a of stepped first notch 182; (d) a second lateral side of the push button portion bears against raised retention boss edge feature 133a; and (e) C-shaped body flexion length distal end 163 is positioned bearing against, or engaging, raised retention boss edge feature 133b. This assembled configuration enables the safety lock push button 164 to be depressed, translating the safety lock push button substantially within the interior of the dispensing actuator cylindrical sidewall 130.

In FIG. 11, a bottom view of the actuation safety lock member 160 operatively assembled within a central portion of the dispensing actuator 120 is shown in an initial locked, child-resistant state, but with the safety lock push button fully depressed in order to enable subsequent rotation of dispensing actuator 120 toward an unlocked, compressible state. In this configuration, the following conditions hold true: (a) safety lock push button portion 164 of actuation safety lock member 160 is depressed through the safety lock member push button passageway 135, such that the first lateral side of the push button portion bears against radiused edge portion 129a of inwardly-tapered edge 129 of wing 122, to facilitate subsequent rotation of dispensing actuator 120 without undesirable impedance between wing 122 and push button 164; and (b) C-shaped body flexion length 162 is inwardly compressed, as actuation safety lock member 160 remains anchored between raised retention boss edge features 133a and 133b. This assembled configuration enables the subsequent rotation of dispensing actuator 160 with respect to bottle cap 170.

In FIG. 12, a bottom view of the actuation safety lock member 160 operatively assembled within a central portion of the dispensing actuator 120 is shown, wherein the safety lock member is shown with push button 164 fully depressed, and the dispensing actuator 120 has been rotated to the unlocked, operative (dispensing) state. In this position, as best illustrated in FIG. 3, dispensing actuator 120 is positioned in a raised position with the wings 122 overlying the corresponding second step 182b of stepped first notch 182 and the second notch 187. In this unlocked state, the dispensing actuator 120 can be selectively compressed, or depressed, to communicate a metered dosage of medicinal composition through dip tube 152, through dispensing pump assembly 150, and through dispensing nozzle extension 138 for discharge, or emission, through nozzle orifice 139 for delivery to the nasal cavity of a user.

Figure 2:
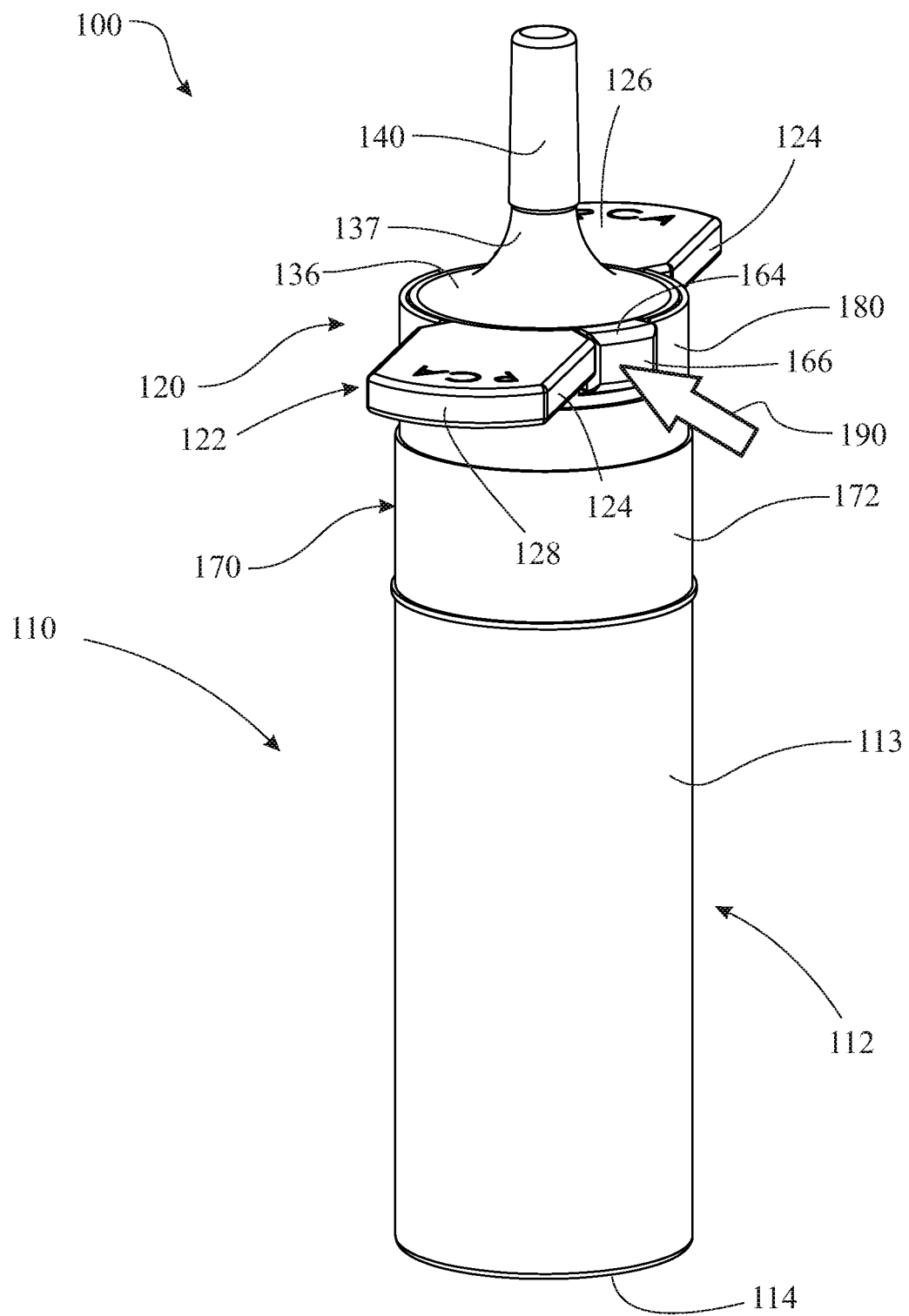
FIG. 2 is an isometric view of the CR nasal sprayer assembly originally introduced in FIG. 1, illustrating the application of an unlocking compression force applied to a safety lock push button.

To reiterate, to place the child resistant nasal sprayer assembly 100 into an unlocked configuration, the user would apply a safety release force 190 to the safety lock push button release force application surface 166 of the safety lock push button 164, as illustrated in FIGS. 2 and 10. This causes the safety lock push button 164 to be repositioned inward. The C-shaped body flexion length 162 provides a biasing force to the safety lock push button 164, which is overcome by the push button safety release force 190. Once the safety lock push button release force application surface 166 of the safety lock push button 164 is depressed to a depth of the interior surface of the sidewall of the bottle cap upper section 182, as shown in FIG. 11, the operator would apply a rotation force 192 to the wing rotational contact surface 124, causing the rotating dispensing actuator 120 to rotate. The rotated dispensing actuator 120 retains the safety lock push button 164 in an unlocked position within the interior of the actuator cylindrical sidewall 130. The actuator wing 122 includes a radiused edge 129a designed and configured to roll against the safety lock push button 164 to help depress the push button should the safety lock push button 164 remain partially proud of the exterior surface of the actuator cylindrical sidewall 130. This enables the dispensing actuator 120 to be compressed, as illustrated in FIG. 4. The operator would subsequently apply the compression discharge force 194 to each of the actuator wings 122, causing the dispensing actuator 120 to slide downward. The downward motion operates the dispensing pump assembly 150 to dispense the medicinal composition from within the bottle interior volume 119 of the bottle 110.

When the rotating dispensing actuator 120 is rotated and returned to a seated position locating the actuator wing 122 within the wing storage notch 182a, the biasing force generated by C-shaped body flexion length 162 drives the safety lock push button 164 through the actuator cylindrical sidewall passageway 135 and into the wing actuation enabling notch 182b, securing the child resistant nasal sprayer assembly 100 against unintended dispensing.

The various components of the child resistant nasal sprayer assembly 100 can be fabricated of any suitable material. For example, the bottle 110 can be fabricated of a clear plastic using a blow molding process. Alternatively, the bottle 110 can be fabricated of a translucent plastic material or an opaque plastic material. In an application where plastic may be incompatible with the medicinal composition, the bottle 110 can be fabricated of a glass, metal, or other suitable material.

The child resistant nasal sprayer assembly 100 is designed to enable exchange of any of the various components. This enables a medical professional, a pharmacist, an end user, or any other party to exchange a part being manufactured in one color with a like part that is manufactured in a second, different color. This enables the end use a way to distinguish the contents of a first bottle from contents contained in a second bottle, where the contents in the first bottle and the contents in the second bottle are different.

Although the above provides a full and complete disclosure of the preferred embodiments of the invention, various modifications, combinations, alternate constructions and equivalents will occur to those skilled in the art. For example, although the invention has been described with reference to a semi-circular ring shaped rotation locking member, alternatively, the rotation locking member may be configured as a sleeve or elongated/wide ring. It is intended that all matters in the foregoing description and shown in the accompanying drawings be interpreted as illustrative and not in a limiting sense. Therefore the above should not be construed as limiting the invention, which is defined by the appended claims and their legal equivalence.

REFERENCE ELEMENT DESCRIPTIONS 100 child resistant (CR) nasal sprayer assembly
110 bottle (generally)
112 bottle body
113 bottle body cylindrical sidewall 114 bottle body bottom wall
116 bottle cap locking feature
119 bottle interior volume
120 rotatable and compressible dispensing actuator
122 dispensing actuator wings
124 wing rotational actuation contact edges
126 wing compression actuation contact surface
127 wing lower surface
128 wing distal edge
129 wing tapered edge
129a wing radiused edge portion
130 dispensing actuator cylindrical sidewall
130a dispensing actuator cylindrical sidewall upper edge
130b dispensing actuator cylindrical sidewall lower edge
130c dispensing actuator cylindrical sidewall opening
130d dispensing actuator cylindrical sidewall exterior surface
130e dispensing actuator cylindrical sidewall interior surface
131 raised retention boss (for anchoring actuation safety lock member)
132 actuator compression stop limit edge
133a first raised retention boss edge feature
133b second raised retention boss edge feature
134 actuator rotation stop limit edge
135 safety lock member push button passageway
136 dispensing actuator upper wall
137 composition dispensing nozzle
138 dispensing nozzle stem extension
139 nozzle orifice
140 dust cap
150 dispensing pump assembly (generally)
150a dispensing pump assembly conduit/passageway
152 dip tube
154 dip tube distal end composition pick up orifice
156 dip tube passageway
160 actuation safety lock member (generally)
161 actuation safety lock member C-shaped body
162 C-shaped body flexion length
162a C-shaped body flexion length convex exterior surface
162b C-shaped body flexion length concave interior surface
163 C-shaped body flexion length distal end
164 C-shaped body push button portion
166 C-shaped body push button portion contact surface
167 C-shaped body push button facet
168 C-shaped body proximal end
170 bottle cap
172 bottle cap base section
174 bottle cap base section cylindrical sidewall
176 bottle cap base section lower edge
178 horizontally-oriented annular transition wall
178a central opening in annular transition wall 178
179 vertically-oriented annular wall/pump retention feature
180 bottle cap upper section
181 upper edge of bottle cap upper section
182 stepped first notch (generally)
182a first, shallow step
182b second, deep step
183 wing vertical compression-resisting horizontal edge of stepped first notch
184 wing clockwise rotation-resisting first vertical edge of stepped first notch
185 wing vertical compression horizontal stop limit edge of stepped first notch
186a wing clockwise rotation-resisting second vertical edge of stepped first notch
186b wing counterclockwise rotation-resisting vertical edge of stepped first notch
187 second notch
188a wing clockwise rotation-resisting vertical edge of second notch
188b wing counterclockwise rotation-resisting vertical edge of second notch
189 wing vertical/axial compression horizontal stop limit edge of second notch
190 safety lock push button release force
192 dispensing actuator counterclockwise rotation force
194 dispensing actuator compression discharge force
199 atomized composition discharge
200 central axis of child resistant nasal sprayer assembly 100

What is claimed is:

1. A child resistant nasal sprayer assembly oriented along a central axis, the child resistant nasal sprayer assembly comprising:

a bottle having a body defined by a cylindrical sidewall extending between a lower end and an opposite upper end, a bottom wall having a periphery contiguous with the cylindrical sidewall lower end, the sidewall upper end defining a bottle body opening, the bottle body defining an interior bottle space containing a dispensable composition;

an actuation safety lock member in the form of a C-shaped body extending between a proximal end and a distal end, a push button feature protruding radially outward from an exterior, convex surface proximate to the proximal end of the C-shaped body, wherein, during use, the structure of the actuation safety lock member enables inward radial flexure along a flexion length of the C-shaped body between the push button feature and the distal end;

a rotatable and compressible dispensing actuator including a central body portion in the form of a cylindrical sidewall having an interior sidewall surface and an opposite exterior sidewall surface, the dispensing actuator central body cylindrical sidewall transitioning, at an upper end thereof, to a dispensing actuator upper wall, the dispensing actuator upper wall transitioning radially inward to a dispensing actuator nozzle having a central dispensing actuator nozzle orifice, a pair of actuator wings extending radially outward from the exterior sidewall surface of the central body portion, the pair of actuator wings circumferentially offset from one another, the central body cylindrical sidewall having an opening extending completely therethrough, the opening sized and shaped to enable extension of the push button feature of the safety lock member therethrough when the dispensing actuator is in a child-resistant locked position, the opposite proximal and distal ends of the safety lock member C-shaped body each bearing against respective edges of a raised safety lock member retention feature protruding radially inward from the interior surface of the central body portion cylindrical sidewall, the exterior surface of the safety lock member C-shaped body flexion length between the push button feature and the distal end bearing against the interior surface of the central body portion cylindrical sidewall when the dispensing actuator is in said child-resistant locked position;

a bottle cap having a base section and an upper section adjoined by an annular transition wall having a plane oriented transverse to a common central axis of the base section and the upper section, the base section having a cylindrical sidewall secured at a lower end thereof about the bottle opening, the annular transition wall defining a central aperture, the upper section of bottle cap having a cylindrical sidewall terminating at an upper edge, the upper edge defining a stepped first notch and a second notch circumferentially offset from the stepped first notch; and a dispensing pump subassembly extending from within the interior bottle space, through the central opening in the bottle cap annular transition wall, and into an interior of the dispensing actuator, the dispensing pump subassembly arranged and configured to dispense a volume of the dispensable composition contained within the bottle body interior space, wherein, upon applying a push button release force to a push button contact surface of the actuation safety lock member C-shaped body, and subsequently rotating the dispensing actuator in a direction toward a lowermost notch of the bottle cap stepped first notch, wherein the dispensing actuator is in an unlocked state, the dispensing actuator may be freely compressed to communicate a volume of the dispensable composition from the interior bottle space, through the dispensing pump subassembly, for emission through an opening of the dispensing actuator nozzle.

2. The child resistant nasal sprayer assembly recited in claim 1, wherein the dispensing actuator wings are circumferentially offset 180° from each other.

3. The child resistant nasal sprayer assembly recited in claim 1, wherein each one of the pair of dispensing actuator wings extends outwardly from the exterior sidewall surface of the central body portion to define an actuator wing radiused edge.

4. The child resistant nasal sprayer assembly recited in claim 1, wherein, the exterior surface of the dispensing actuator central body portion cylindrical sidewall is in frictional engagement with an interior surface of the upper section cylindrical sidewall.

5. The child resistant nasal sprayer assembly recited in claim 4, wherein, during a composition dispensing operation, the lower edge of the dispensing actuator cylindrical sidewall engages an upper surface of the bottle cap transverse annular wall to limit downward translation of the dispensing actuator.

6. The child resistant nasal sprayer assembly recited in claim 1, wherein the push button portion of the actuation safety lock member C-shaped body transitions to the push button contact surface via a tapered facet.

7. The child resistant nasal sprayer assembly recited in claim 1, wherein, upon concurrently depressing the push button inwardly and rotating the dispensing actuator from a locked state to an unlocked state, compression of the flexion length of the actuation safety lock member C-shaped body urges flexure of the flexion length.

8. The child resistant nasal sprayer assembly recited in claim 7, wherein, upon rotating the dispensing actuator back from the unlocked state to the child resistant locked state, the flexion length of the actuation safety lock member C-shaped body is decompressed and the push button portion is urged outwardly through the opening in the cylindrical sidewall of the dispensing actuator.

9. The child resistant nasal sprayer assembly recited in claim 1, wherein the dispensing actuator cylindrical sidewall is slidably and rotationally assembled to the cylindrical upper section of the bottle cap, wherein, in operation, the safety lock member push button is depressed to clear the interior surface of the cylindrical sidewall of the bottle cap upper section, thereby enabling rotation of the dispensing actuator relative to the bottle cap, to a position urging the safety lock member push button against the interior surface of the bottle cap upper section cylindrical sidewall to enable downward axial translation of the dispensing actuator upon application of a compressive force to upper surfaces of the respective dispensing actuator wings, the compression causing the dispensing actuator to slide downwardly within the bottle cap upper section to engage the dispensing pump and thereby discharge a volume of the composition, in the form of a mist, through the dispensing actuator nozzle orifice.

10. The child resistant nasal sprayer assembly recited in claim 1, wherein the pair of wings further comprise respective planar wing compression contact surfaces oriented perpendicular to the central axis of the child resistant nasal sprayer assembly.

11. The child resistant nasal sprayer assembly recited in claim 10, wherein the dispensing pump subassembly is supported by the bottle cap.

12. The child resistant nasal sprayer assembly recited in claim 11, wherein the dispensing pump subassembly is supported by a vertically-oriented annular wall disposed about a perimeter of the central opening in the bottle cap annular transition wall and extending upwardly from the upper surface of the bottle cap annular transition wall.

* * * * *